United States Patent [19]

Chen

[11] Patent Number: 5,458,888
[45] Date of Patent: Oct. 17, 1995

[54] CONTROLLED RELEASE TABLET FORMULATION

[75] Inventor: Chih-Ming Chen, Cooper City, Fla.

[73] Assignee: Andrx Pharmaceuticals, Inc., Fort Lauderdale, Fla.

[21] Appl. No.: 205,005

[22] Filed: Mar. 2, 1994

[51] Int. Cl.⁶ .............................. A61K 9/22; A61K 9/32
[52] U.S. Cl. ..................... 424/464; 424/458; 424/465; 424/468; 424/469; 424/482; 424/484; 424/494; 424/497
[58] Field of Search ..................... 424/464, 465, 424/458, 468, 482, 497, 501, 469, 486

[56] References Cited

U.S. PATENT DOCUMENTS

| | | | |
|---|---|---|---|
| 3,108,046 | 10/1963 | Harbit | 167/82 |
| 4,380,534 | 4/1983 | Fukui et al. | 424/38 |
| 4,415,547 | 11/1983 | Yu et al. | 424/19 |
| 4,432,965 | 2/1984 | Keith et al. | 424/19 |
| 4,684,516 | 8/1987 | Bhutani | 424/19 |
| 4,710,384 | 12/1987 | Rotman | 424/465 |
| 4,755,386 | 7/1988 | Hsiao et al. | 424/435 |
| 4,874,614 | 10/1989 | Becker | 424/465 |
| 5,085,033 | 2/1992 | Graham | 424/454 |
| 5,139,790 | 8/1992 | Snipes | 424/435 |

FOREIGN PATENT DOCUMENTS

| | | |
|---|---|---|
| 8404674 | 12/1984 | WIPO. |
| 8604817 | 8/1986 | WIPO. |
| 9315723 | 8/1993 | WIPO. |

*Primary Examiner*—Thurman K. Page
*Assistant Examiner*—James M. Spear
*Attorney, Agent, or Firm*—Hedman, Gibson & Costigan

[57] ABSTRACT

The present invention provides a controlled release dosage form which may be made using a blend having an internal drug containing phase and an external phase which comprises a polyethylene glycol polymer which has a weight average molecular weight of from 3000 to 10000. The dosage formulation may be pressed into tablets or it may be formed directly into discrete orally administrable shapes by pressing the blend into a cavity which is sized to accept a volume of the blend which is equivalent to one dosage unit. A plurality of cavities may be formed in a strip of plastic which may be sealed after the blend of the invention is pressed in place to form a plurality of unit doses of a drug.

10 Claims, 1 Drawing Sheet

CONTROLLED RELEASE TABLET FORMULATION

BACKGROUND OF THE INVENTION

The present invention is concerned with a controlled release dosage formulation that is based on the combination of a relatively hard, internal coated core material that contains the active medicament and a relatively soft, external phase that surrounds the internal phase and forms the external surface of the dosage formulation. The external phase comprises a water soluble polymer which may contain up to 10 wt % of water insoluble additives.

In order to provide a controlled release product, a water insoluble material such as a cellulose polymer or a wax has been used to coat discrete drug containing units such as drugs or crystals in order to resist the action of the fluids in the gastrointestinal tract. These coatings have resulted in the production of satisfactory pellets or granules that would usually be placed in a gelatin capsule because if a tablet was made by compressing the cellulose polymer or wax coated pellets, the coating would either rupture or become so deformed that the uniformity of any wax coating would be adversely affected.

The prior art has used microcrystalline cellulose to coat sustained release pellets (SR) pellets to provide cushioning and has used a major portion of cushioning agent to minimize the breakage of the SR pellets.

SUMMARY OF THE INVENTION

The present invention is directed to a controlled release dosage form which may be made using a blend having (a) an internal coated core material drug containing slow release drug pellets or particles and (b) an external phase which comprises a polyethylene glycol polymer which has a weight average molecular weight of from 3000 to 10000. The dosage formulation may be pressed into tablets or it may be formed directly into discrete orally administrable shapes by using heat to liquefy the polyethylene glycol polymer and causing the liquified blend to flow into a cavity which is sized to accept a volume of the blend which is equivalent to one dosage unit. A plurality of cavities may be formed in a strip of plastic which may be sealed after the blend of the invention is pressed in place to form a plurality of unit doses of a drug.

Accordingly it is a primary object of this invention to provide a novel controlled release dosage formulation.

It is also an object of this invention to provide a novel tabletted formulation which is made by pressing out the tablets from a formulation having a drug containing internal phase and an external phase which comprises a high molecular weight polyethylene glycol.

It is also an object of this invention to provide a novel controlled release pharmaceutical dosage unit which does not require the use of additional cushioning agents.

These and other objects of the invention will become apparent from a review of the appended specification.

DETAILED DESCRIPTION OF THE INVENTION

Figure 1:
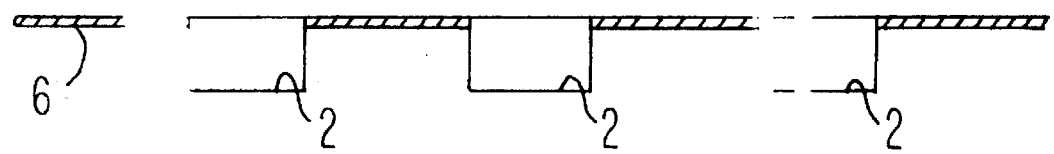
FIG. 1 is a cross-section of the plastic strip cavity container in which dosage units according to the invention may be formed.

The controlled release dosage unit of the invention comprises an external phase which is a high molecular weight polyethylene glycol. It is to be understood that the term "external phase" is used to describe the outermost material in the tablet of the invention although that material does extend into the interior and forms a cushioning matrix which surrounds the internal coated core materials. The internal coated core material may be pellets, granules, microtablets, crystals or mixtures thereof the external phase may comprise of up to 10 wt % of a water insoluble additive i.e. 1–10 wt % which may be a hydrophobic agent such as magnesium stearate, fatty acids.

Pelleting, granulation and tableting processes are well known and may be used to provide immediate release and sustained release doses of drugs for use as the relatively hard, intend coated material. Procedures for making pellets are described in Pharmaceutical Pelletization Technology, Ghebre-Sellasie Ed. Marcel Dekker, Inc., N.Y. 1989, which is incorporated by reference. The techniques of preparing granulations and tablets are well known and are described in Remingtons Pharmaceutical Sciences, 1990 Ed., which is incorporated by reference.

Generally, the pellets are made by agitation, compaction, layering or globalation processes. The release properties of the pellets will depend on the additives and coatings which are employed. Examples of the techniques of preparing sustained release pellets are described in Aqueous Polymeric Coating for Pharmaceutical Dosage Forms, J. W. Mc Carthy, Ed., Marcel Dekker, Inc., NY (1989) and Eudragit RL/RS Technical Application Pamphlet (Info RL/RS 12e)(2/90) and which are incorporated by reference.

If desired, pigmented or dyed non-enteric film coatings may be applied to the tabletted product to provide a colored tablet. If desired, a compatible pigment may be added to the coated core material or to the external water soluble polymer. The use of colorants is described in Modern Pharmaceutics, Vol. 7, Banker et al Marcel Dekker, Inc., N.Y. (1979).

The internal core different populations of pellets. Each pellet contains a core in which there is a drug. The core may be coated with a protective film which is water insoluble and either is erodible in gastrointestinal fluid or is a water insoluble, water permeable film forming polymer material. The thickness of the coating of the core is uniform within a given population of pellets and the coating thickness determines the lag time before the drug is released in the gastrointestinal tract.

The pellets may be made with a core which contains a drug and a water soluble modulating agent or osmotic agent which may be any water soluble, non-toxic, pharmaceutically acceptable salt that competes with the drug in the core for the gastrointestinal fluid for the water that diffuses through the water permeable polymer material that is used to coat the core of the pellet. As the water soluble modulating agent dissolves within the core of the pellet, the concentrated solution of the water soluble modulating agent increases the osmotic pressure between the core of the pellet and the aqueous environment outside of the core to create a flux which draws more aqueous fluid into the core and causes the pellet to swell. As the pellets swell the water permeable polymer material tends to stretch and become thinner which increases the rate of release of the drug into the gastrointestinal tract, a swelling agent may also be included in the pellets.

The osmotic agent may be selected from alkali metal chlorides such as sodium chloride and potassium chloride. Other inorganic salts such as sodium dihydrogen phosphate, or organic acids such as citric acid, malic acid, maleic acid, fumaric acid and the like may be utilized in the practice of the invention.

The pH of various portions of the gastrointestinal tract is variable and the transit time of solids through the gastrointestinal tract is also variable between individuals and within the same individual under different circumstances. To insure that the variation ion pH do not defeat the objective of preset release time intervals, the coating of the pellets may be made of material that is substantially pH independent in its properties within the pH that is encountered in the gastrointestinal tract. The coating may be made of water permeable, water insoluble, film forming polymer materials such as cellulose ether derivatives, acrylic resins, copolymers of acrylic acid and methacrylic acid esters. Combined with the polymer material may be a hydrophobic agent which may be a fatty acid of 10 or more carbon atoms, wax or the salts of a fatty acid or 10 or more carbon atoms such as magnesium stearate or calcium stearate. The particular hydrophobic agent may be a mixture of stearates which contain other fatty acids because the product is derived from a natural source. The purpose of the hydrophobic agent is to reduce the permeability of the water insoluble, water permeable polymer to water by adding from 25% to 50% by weight of the hydrophobic agent to said polymer based on the total combined weight of the hydrophobic agent and said polymer. Small amounts of stearates will reduce tackiness and very large amounts will reduce water permeability. Plasticizers such as triacetin may be added to the water insoluble polymer to control any brittleness in the polymer.

With regard to the composition of the different populations of pellets, for example a rapid release pellet may be made with 20 to 30% by weight of hydrophobic agent based on the total weight of said polymer and said hydrophobic agent. Slow release pellets may be made with from 40 to 60% by weight of hydrophobic agent based on the total weight of said polymer and said hydrophobic agent. The addition of a plasticizer as described above is optional and the amount which is employed will depend on the particular plasticizer. In the case of triacetin, for 25 to 35% by weight based on the combined weight of said polymer and said plasticizer may be employed.

The pellets may be made according to the procedures of U.S. Pat. No. 5,260,068 which is incorporated by reference. In the alternative, the teachings of U.S. Pat. No. 5,260,069, which is also incorporated by reference, may be used to prepare pellets.

The dosage formulation may be pressed into tablets by first pouring a molten blend of the dosage composition into a tablet mold and applying a suitable die to form the upper surface of the tablet. Thereafter the tablet may be ejected from the mold by applying pressure to the bottom of the tablet. In the alternative, a dosage unit may be formed directly into discrete orally administrable shapes by pressing the blend into a cavity which is sized to accept a volume of the molten blend which is equivalent to one dosage unit. A plurality of cavities may be formed in a strip of plastic which may be sealed with a metal foil layer using the technique which is conventionally referred to as blister packaging to form the upper surface of the dosage unit. This one step technique of forming a dosage unit in a plastic strip which is adaptable to the single dose packaging provides significant savings in cost, time and handling as well as avoiding the possibility of contamination due to the handling which is required when tablets are packaged.

The method of forming a pharmaceutical dosage unit in a strip package is based on the following steps:

(a) forming a molten blend which comprises an active drug which may be in the form of sustained release pellets and a high molecular weight polyethylene glycol;

(b) providing an elongated strip of packaging material having a plurality of voids which are sized to accepted a volume of said molten blend which is equivalent to one therapeutic dose of the drug in said molten blend;

(c) filling said plurality of voids in said elongated strip of packaging material with said molten blend;

(d) allowing said molten blend in step (c) to solidify; and (e) sealing said solidified dosage units in said elongated strip of packaging material to simultaneously form the top surface of the dosage unit and to seal the strip package.

FIG. 1 shows a cross-section of a portion of a strip package which has a plurality of cavities 2 formed in the surface 6 of the strip package for receiving the molten blend. A sealing member 4 is shown in sealing engagement with the surface 6 of the strip package.

The drugs that may be prepared in the controlled release dosage formulation of the invention include but are not limited to antibiotics, tranquilizers, agents which act on the heart, liver, kidneys, central nervous system, muscles, contraceptives, hormonal agents, antineoplastic agents or combinations of therapeutically complimentary drugs. These drugs are described in the Physicians Desk Reference, 1994 Ed., which is incorporated by reference.

The different pellets in the internal phase of the control release dosage formulation of the invention may be prepared to dissolve promptly in the gastrointestinal tract or they may be prepared to resist dissolution at pH's of 1 to 7.5. One population of pellets may be designed for instant release and one or more populations may be designed for subsequent release according to the half-life of the minimum effective concentration of the particular drug in the body.

The following examples are added to illustrate the invention and are not to be construed as limiting the scope of the invention.

EXAMPLE 1

A coating pan is charged with the following:

| | |
|---|---:|
| Eudragit L 30 D 30% | 16.7 kg |
| (aqueous dispersion of poly- | (5.0 solid polymer) |
| methacrylic acid, ehtylacrylate) | |
| (MW weight average 250,000) | |
| Acetyl triethyl citrate | 0.5 kg |
| Talc | 2.5 kg |
| Water | 12.3 kg |
| Acetylsalicylic acid crystals (ASA) | 50.0 kg |

The ASA crystal is loaded into a coating pan and is spray-coated with a suspension of the other components. The temperature of the inlet air is 54°–60° C. and the temperature of the exhaust air is 32° C. After about 105 minutes the coated ASA crystals are formed. The coated ASA crystals are mixed with an equal weight of polyethylene glycol (wt av. Mol. wt 3350, Carbowax 3350) at about 50° C. to form a molten blend. The molten is formed into tablets using a tablet mold.

EXAMPLE 2

80 grams of sodium chloride and 24 grams of polyvinylpyrrolidone are dissolved in 1.2 kilograms of water and 400 grams of pulverized diltiazem hydrochloride are suspended therein with agitation.

In a fluidized coming bed, 400 grams of starch/sugar seeds (30/50 mesh) are suspended in warm air and spray coated with the diltiazem suspension until the seeds are uniformly coated with the diltiazem.

Magnesium stearate in isopropyl alcohol (25% by weight) is mixed with Eudragit NE30D (Rohm Pharma, Weitersradt, Germany) which is a trademarked 30% aqueous dispersion of poly (ethyl acrylate methyl acrylate)(2:1 wt average mol et 800,000) at a weight ratio of 3 to 1. A sufficient amount of the polymer suspension is sprayed onto the active cores to provide a particular film coating thickness to achieve a particular lag time and rate of release for a population of pellets. The coated pellets are dried at 50° C. for 2 hours to assure complete removal of moisture to stabilize the core contents.

The procedure is repeated with at least one more batch using a different coating thickness to have a different lag time and rate of release. In this example two populations are prepared, one with a 10% weight gain of coating and one with a 30% weight gain of coating.

The combined pellets are dispersed in melted polyethylene glycol at a temperature of 50° C. The polyethylene glycol has a weight average molecular weight of 3350 (Carbowax 3350) and is used at a weight ratio of 10 g. of pellets to 10 g. of polyethylene glycol.

The suspension of the pellets in the molten polyethylene glycol is maintained in a homogeneous state by the use of gentle agitation and by maintaining the suspension of pellets at about 50° C. The molten mixture is poured into tablet shaped molds and is gently compressed (1 psi) to form tablets having convex surfaces on the top and bottom of the tablet. The tablets are ejected from the mold by a piston that lifts the molded tablet from the bottom of the mold.

EXAMPLE 3

Pellets were made from the following components:

| | |
|---|---|
| Nifedipine | 200 g. |
| Explotab (starch glycolate) | 200 g. |
| Polyvinylpyrrolidone | 20 g. |
| Ethanol | 1800 g. |

The solid components were dispersed in the ethanol until uniform. The suspension was then spray coated onto 400 g. of sugar spheres (size 40 to 50 mesh) in a fluidized coating bed equipped with a Worster column. Six hundred grams of the nifedipine pellets are then coated with a polymer suspension which consists of:

| | |
|---|---|
| Ethylcellulose | 90 g. |
| Eudragit S100 (ethacrylic acid polymer) | 45 g. |
| Magnesium stearate | 15 g. |
| Ethanol | 1800 g. |

When 25%, 50% and 75% of the coatings are consumed, the coating machine is stopped and 50 g is collected. Then coating is continued until all of the coating material is consumed. The pellets were then formed into tablets using a high molecular weight polyethylene glycol according to the procedure of Example 1.

I claim:

1. A control led release pharmaceutical dosage formulation which consists essentially of:
   (a) as the internal phase, a pelleted coated core material containing an active medicament, and
   (b) a water soluble external phase which extends around and coats said internal phase comprises a polyethylene glycol having a weight average molecular weight between 3,000 and 10,000.

2. A controlled release pharmaceutical dosage formulation as defined in claim 1 wherein the coated core materials in the internal phase are a plurality of pellets which release said drug into the gastrointestinal tract at different times.

3. A controlled release dosage form as define in claim 2 wherein the active drug is selected from the group consisting of nifedipine and diltiazem.

4. A controlled release pharmaceutical dosage formulation as defined in claim 2 wherein the pellets comprise different populations provided with a coating that causes the drug to be released at different times into the gastrointestinal tract than other populations of pellets to thereby provide a plurality of sequential therapeutic releasing events with each population providing a different time of release of said drug.

5. A controlled release pharmaceutical dosage formulation as defined in claim 2 in which the pellets of each population of pellets differs from the other populations in the thickness of the coatings.

6. A controlled release pharmaceutical dosage formulation as defined in claim 2 wherein the core of each pellet includes a swelling agent.

7. A controlled release pharmaceutical dosage formulation as defined in claim 2 in which the film forming, water insoluble polymer material are selected from the group consisting of copolymers of acrylic and methacrylic acid esters, copolymers of acrylic and methacrylic acid esters with quaternary ammonium groups, cellulose ethers and acrylic resins.

8. A method of forming a pharmaceutical dosage unit, said method comprising:
   (a) forming a molten blend which comprises as the internal phase, a pelleted coated core material containing an active medicament, and (b) a water soluble external phase which extends around and coats said internal phase which comprises a polyethylene glycol having a weight average molecular weight between 3,000 and 10,000
   (b) providing an elongated strip of packaging material having a plurality of voids which are sized to accept a volume of said molten blend which is equivalent to one therapeutic dose of the drug in said molten blend;
   (c) filling said plurality of voids in said elongated strip of packaging material with said molten blend;
   (d) allowing said molten blend in step (c) to solidify; and
   (e) sealing said solidified dosage units in said elongated strip of packaging material to simultaneously form the top surface of the dosage unit and to seal the strip package.

9. A controlled release dosage form as defined in claim 2 in which there are at least two populations of pellets.

10. A controlled release pharmaceutical dosage formulation which consists of:
    (a) as the internal phase, a coated core material containing an active medicament, and (b) a water soluble external phase which extends around and coats said internal phase comprises a polyethylene glycol having a weight average molecular weight between 3,000 and 10,000.

* * * * *